United States Patent
Hothi et al.

(10) Patent No.: US 11,499,972 B2
(45) Date of Patent: Nov. 15, 2022

(54) METHODS AND PANELS OF COMPOUNDS FOR CHARACTERIZATION OF GLIOBLASTOMA MULTIFORME TUMORS AND CANCER STEM CELLS THEREOF

(71) Applicant: Swedish Health Services, Seattle, WA (US)

(72) Inventors: Parvinder Hothi, Kent, WA (US); Charles Cobbs, Mercer Island, WA (US)

(73) Assignee: Swedish Health Services, Seattle, WA (US)

(*) Notice: Subject to any disclaimer, the term of this patent is extended or adjusted under 35 U.S.C. 154(b) by 277 days.

(21) Appl. No.: 15/760,612

(22) PCT Filed: Sep. 14, 2016

(86) PCT No.: PCT/US2016/051669
§ 371 (c)(1),
(2) Date: Mar. 15, 2018

(87) PCT Pub. No.: WO2017/048800
PCT Pub. Date: Mar. 23, 2017

(65) Prior Publication Data
US 2018/0252717 A1 Sep. 6, 2018

Related U.S. Application Data

(60) Provisional application No. 62/218,759, filed on Sep. 15, 2015.

(51) Int. Cl.
*G01N 33/574* (2006.01)
*A61K 45/06* (2006.01)
(Continued)

(52) U.S. Cl.
CPC ........... *G01N 33/574* (2013.01); *A61K 31/00* (2013.01); *A61K 45/06* (2013.01); *C12N 5/0695* (2013.01);
(Continued)

(58) Field of Classification Search
CPC ......... G01N 33/574; G01N 2800/7028; A61K 31/00; A61K 45/06
(Continued)

(56) References Cited

U.S. PATENT DOCUMENTS

| 8,993,231 B2 | 3/2015 | Claudio et al. |
| 9,316,632 B2 | 4/2016 | Claudio et al. |

(Continued)

FOREIGN PATENT DOCUMENTS

| WO | WO-2012172069 A1 | 12/2012 |
| WO | WO-2013126993 A1 | 9/2013 |

(Continued)

OTHER PUBLICATIONS

Balvers R et al., ABT-888 enhances cytotoxic effects of temozolomide independent of MGMT status in serum free cultured glioma cells. Journal of Translational Medicine13:74 (2015).
(Continued)

*Primary Examiner* — Jeremy C Flinders
(74) *Attorney, Agent, or Firm* — Wilson Sonsini Goodrich & Rosati

(57) ABSTRACT

A method of characterizing a glioblastoma multiforme (GBM) stem cell (GSC), comprising culturing the GSC to provide a culture, contacting a first set of aliquots of the culture with individual compounds selected from a panel of compounds, identifying two or more of the selected compounds that cause more than a threshold level of cell death in the first set of aliquots, and characterizing the GSC as suitable for treatment with one or more combinations comprising the two or more identified compounds. A panel of
(Continued)

chemical compounds, the compounds selected by a method comprising surgically resecting the tumor, culturing a GSC derived from GBM tissue derived from a GBM tumor, contacting aliquots thereof with individual compounds selected from a panel of compounds, and identifying two or more of the selected compounds that cause more than a threshold level of cell death in the aliquots, thereby identifying the compounds.

8 Claims, 8 Drawing Sheets

(51) Int. Cl.
*A61K 31/00* (2006.01)
*C12Q 1/00* (2006.01)
*C12N 5/095* (2010.01)

(52) U.S. Cl.
CPC ....... *C12Q 1/00* (2013.01); *G01N 2800/7028* (2013.01)

(58) Field of Classification Search
USPC .......................................................... 506/10
See application file for complete search history.

(56) References Cited

U.S. PATENT DOCUMENTS

| | | | |
|---|---|---|---|
| 9,575,055 | B2 | 2/2017 | Gevaert et al. |
| 10,240,121 | B2 | 3/2019 | Gevaert et al. |
| 10,466,232 | B2 | 11/2019 | Gevaert et al. |
| 11,149,248 | B2 | 10/2021 | Gevaert et al. |
| 2010/0287638 | A1 | 11/2010 | Dirks et al. |
| 2011/0178046 | A1 | 7/2011 | Ross et al. |
| 2011/0301221 | A1 | 12/2011 | Lin et al. |
| 2012/0039915 | A1 | 2/2012 | Liu et al. |
| 2012/0245045 | A1 | 9/2012 | Kislin et al. |
| 2013/0295198 | A1 | 11/2013 | Claudio et al. |
| 2013/0323300 | A1 | 12/2013 | Olin et al. |
| 2014/0154735 | A1 | 6/2014 | Sundstrom et al. |
| 2014/0255471 | A1 | 9/2014 | Gmeiner et al. |
| 2015/0030583 | A1 | 1/2015 | Moore et al. |
| 2015/0148390 | A1 | 5/2015 | Scheffler et al. |
| 2015/0290300 | A1 | 10/2015 | Kaur et al. |
| 2019/0125772 | A1 | 5/2019 | Ho et al. |
| 2021/0389299 | A1 | 12/2021 | Hothi et al. |

FOREIGN PATENT DOCUMENTS

| WO | WO-2017023277 A1 | 2/2017 |
|---|---|---|
| WO | WO-2017048800 A1 | 3/2017 |

OTHER PUBLICATIONS

Davis; Mary Elizabeth: Glioblastoma: Overview of Disease and Treatment. Clinical Journal of Oncology Nursing. Supplement to vol. 20(5):7 pages (2016).

European Patent Application No. EP15900545.3 Extended European Search Report dated Dec. 18, 2018.
European Patent Application No. EP16847202.5 Office Action dated Oct. 31, 2019.
Gal H et al., A rapid assay for drug sensitivity of glioblastoma stem cells. Biochemical and Biophysical Research Communications 358:908-913 (2007).
Hothi et al., High-throughput chemical screens identify disulfiram as an inhibitor of human glioblastoma stem cells. Oncotarget 3(10):1124-1136 (2012).
Jiang et al., Novel anti-glioblastoma agents and therapeutic combinations identified from a collection of FDA approved drugs. Journal of Translational Medicine 12(1):13ff (2014).
PCT/US2016/051669 International Preliminary Report on Patentability dated Mar. 29, 2018.
Sami et al.: Targeting the PI3K/AKT/mTOR signaling pathway in glioblastoma: novel therapeutic agents and advances in understanding. Tumor Biology. 34(4):1991-2002 (2013).
Schmidt et al., Comparative drug pair screening across multiple glioblastoma cell lines reveals novel drug-drug interactions. Neuro-Oncology 15(11) 1469-1478 (2013).
U.S. Appl. No. 15/749,416 Office Action dated Jun. 27, 2019.
U.S. Appl. No. 15/749,416 Office Action dated Mar. 13, 2020.
Visnyei et al., A molecular screening approach to identify and characterize inhibitors of glioblastoma stem cells. Molecular Cancer Therapeutics 10(10):1818-1828 (2011).
Binello et al., Targeting glioma stem cells: A novel framework for brain tumors. Cancer Science 102(11):1958-1966 (2011).
Cobbs et al., Methods for the detection of Cytomegalovirus in Glioblastoma cells and tissues. Methods in Molecular Biology, Chapter 11, 1119:165-196 (2014).
Friedl and Wolf, Tumour-cell invasion and migration: Diversity and escape mechanisms. Nature Reviews Cancer 3(5):362-374 (2003).
Krex et al., Long-term survival with glioblastoma multiforme. Brain 130(10):2596-260 (2007).
PCT/US2015/043270 International Preliminary Report on Patentability dated Feb. 15, 2018.
PCT/US2015/043270 International Search Report and Written Opinion dated Oct. 23, 2015.
PCT/US2016/051669 International Search Report and Written Opinion dated Dec. 1, 2016.
Pollard et al., Glioma stem cell lines expanded in adherent culture have tumor-specific phenotypes and are suitable for chemical and genetic screens. Cell Stem Cell 4(6):568-580 (2009).
Stupp and Weber, The Role of radio- and chemotherapy in Glioblastoma. Onkologie 28(6-7):315-317 (2005).
Stupp et al., Radiotherapy plus concomitant and adjuvant temozolomide for glioblastoma. The New England Journal of Medicine 352(10):987-996 (2005).
Wick et al., Pathway inhibition: emerging molecular targets for treating glioblastoma. Neuro-oncology 13(6):566-579, 2011.
European Patent Application No. EP16847202.5 Office Action dated Dec. 18, 2020.
Liu et al.: Novel Therapies for Glioblastoma. Neurology and Neuroscience Reports. 20(19):1-12 (2020).
U.S. Appl. No. 15/749,416 Office Action dated Jul. 23, 2020.

METHODS AND PANELS OF COMPOUNDS FOR CHARACTERIZATION OF GLIOBLASTOMA MULTIFORME TUMORS AND CANCER STEM CELLS THEREOF

CROSS-REFERENCE

This patent application claims the benefit of U.S. Provisional Patent Application Ser. No. 62/218,759, filed Sep. 15, 2015, which is incorporated herein by reference in its entirety.

CROSS-REFERENCE

This application is a U.S. National Stage entry of International Application No. PCT/US16/51669, filed Sep. 14, 2016, which is hereby incorporated by reference in its entirety.

BACKGROUND OF THE INVENTION

Glioblastoma multiforme (GBM), the most common form of primary brain tumor in adults, remains a generally incurable and rapidly fatal disease. This is largely due to the ability of GBM to recur at an average of nine months following primary therapy and, following recurrence, afford an average survival time of only six months. It is evident that even after decades of intense clinical and basic research, a diagnosis of GBM remains, in the large majority of cases, a terminal diagnosis.

SUMMARY OF THE INVENTION

In an embodiment, disclosed is a method of characterizing a glioblastoma multiforme (GBM) stem cell, comprising culturing the GBM stem cell to provide a culture, contacting a first set of aliquots of the culture with individual compounds selected from a panel of compounds, identifying two or more of the selected compounds that cause more than a threshold level of cell death in the first set of aliquots, and characterizing the GBM stem cell as suitable for treatment with one or more combinations comprising the two or more identified compounds.

In an embodiment, the panel comprises at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, or all, of the following compounds: AZD-7762; AZD-8055; BEZ-235; BGT-226; MG-132; NVP-AUY-922; obatoclax; PIK-75; PKI-587; staurosporine; YM155; 10-hydroxycamptothecin; anisomycin; β-peltatin; emetine; gambogic acid; mebendazole; ouabain; peruvoside; phenethyl caffeate; podophyllin acetate; pyrvinium pamoate; and thiram.

In an embodiment, the panel further comprises one or more of the following 76 compounds: albendazole, aprepitant, atorvastatin calcium, auraofin, bleomycin, bortezomib, brompheniramine maleate, captropril, carboplatin, celecoxib, chloroquine, cidovofir, cladribine, clofarabine, clofazimine, clomipamine, clonidine, colchicine, cyclophosphamide, cytarabine, dactinomycin, daunorubicin, digoxin, disulfiram, docetaxel, doxorubicin, erlotinib, ethacrynic acid, epirubicin, etoposide, fludarabine phosphate, fluorouracil, fluphenazine, fluvastatin, gemcitabine, haloperidol, homoharringtonine, hydroxychloroquine, idarubicin, irinotecan, itraconazole, ketoconazole, lomustine, lovastatin, mefloquine, melphalan, memantine, metformin, methotrexate, methylene blue, minoxidil, mitomycin C, mitoxantrone, mycophenolate mofetil, nelfinavir, nisoldipine, paclitaxel, pindolol, pitavastatin, rosuvastatin calcium, sertaline, simvastatin, sirolimus, sorafenib, sodium tetradecyl sulfate, sunitinib malate, temozolomide, teniposide, topotecan, trifluoperazine, valganciclovir, valproic acid, vinblastine sulfate, vincristine sulfate, vinorelbine and vorinostat. In an embodiment, the panel comprises at least 10 of the following anti-neoplastic/chemotherapeutic compounds: bortezomib, clofarabine, cytarabine, dactinomycin, daunorubicin, doxorubicin, erlotinib, epirubicin, etoposide, fludarabine phosphate, gemcitabine, irinotecan, melphalan, methotrexate, mitomycin C, mitoxantrone, paclitaxel, sorafenib, sunitinib, temozolomide, teniposide, topotecan, vinblastine sulfate, vincristine sulfate and vinorelbine, at least 10 of the following additional compounds: albendazole, aprepitant, atorvastatin calcium, auraofin, celecoxib, chloroquine, cidovofir, clofazimine, clomipamine, clonidine, colchicine, digoxin, fluphenazine, fluvastatin, haloperidol, homoharringtonine, itraconazole, lovastatin, mefloquine, metformin, methylene blue, minoxidil, mycophenolate mofetil, nelfinavir, pindolol, rosuvastatin calcium, sertaline, simvastatin, sirolimus, sodium tetradecyl sulfate, trifluoperazine, valganciclovir, valproic acid and vorinostat, and disulfiram. In an embodiment, the GBM stem cell is derived from GBM tumor tissue, and the culturing comprises mechanically dissociating the GBM tissue, adding one or more dissociation enzymes to the GBM tissue, incubating the tissue to facilitate digestion of the tissue by the one or more enzymes, obtaining a suspension of cells from the digested tissue, and propagating the cells in stem cell culture medium to provide the culture. In an embodiment, the dissociation enzyme is ACCUTASE. In an embodiment, the incubating takes place at a temperature range between 35° C. and 39° C. In an embodiment, the incubating takes place at about 37° C. In an embodiment, the threshold level of cell death is about 50%. In an embodiment, at least one of the one or more combinations comprises at least one anti-neoplastic/chemotherapeutic compound and at least one additional compound. In an embodiment, the identifying step further comprises: from the identified two or more selected compounds, further selecting at least two compounds as preferred compounds based on at least one of the following characteristics: overall level of cell death caused in the first set of aliquots; known ability to cross the blood-brain barrier in a GBM patient; and known likely side effects to a GBM patient, and the characterizing step further comprises characterizing the GBM stem cell as suitable for treatment with one or more combinations of the preferred compounds.

In an embodiment, a method of characterizing a glioblastoma multiforme (GBM) stem cell, comprising culturing the GBM stem cell to provide a culture, contacting a first set of aliquots of the culture with individual compounds selected from a panel of compounds, wherein at least one of the selected compounds is an anti-neoplastic/chemotherapeutic compound, identifying two or more of the selected compounds that cause more than a threshold level of cell death in the first set of aliquots, and characterizing the GBM stem cell as suitable for treatment with one or more combinations comprising the two or more identified compounds is disclosed.

In an embodiment, the panel comprises at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, or all, of the following compounds: AZD-7762; AZD-8055; BEZ-235; BGT-226; MG-132; NVP-AUY-922; obatoclax; PIK-75; PKI-587; staurosporine; YM155; 10-hydroxycamptothecin; anisomycin; β-peltatin; emetine; gambogic acid; mebendazole; ouabain; peruvoside; phenethyl caffeate; podophyllin acetate; pyrvinium pamoate; and thiram.

In an embodiment, the panel further comprises one or more of the following 76 compounds: albendazole, aprepitant, atorvastatin calcium, auraofin, bleomycin, bortezomib, brompheniramine maleate, captropril, carboplatin, celecoxib, chloroquine, cidovofir, cladribine, clofarabine, clofazimine, clomipamine, clonidine, colchicine, cyclophosphamide, cytarabine, dactinomycin, daunorubicin, digoxin, disulfiram, docetaxel, doxorubicin, erlotinib, ethacrynic acid, epirubicin, etoposide, fludarabine phosphate, fluorouracil, fluphenazine, fluvastatin, gemcitabine, haloperidol, homoharringtonine, hydroxychloroquine, idarubicin, irinotecan, itraconazole, ketoconazole, lomustine, lovastatin, mefloquine, melphalan, memantine, metformin, methotrexate, methylene blue, minoxidil, mitomycin C, mitoxantrone, mycophenolate mofetil, nelfinavir, nisoldipine, paclitaxel, pindolol, pitavastatin, rosuvastatin calcium, sertaline, simvastatin, sirolimus, sorafenib, sodium tetradecyl sulfate, sunitinib, temozolomide, teniposide, topotecan, trifluoperazine, valganciclovir, valproic acid, vinblastine sulfate, vincristine sulfate, vinorelbine and vorinostat. In an embodiment, the panel comprises at least 10 of the following anti-neoplastic/chemotherapeutic compounds: bortezomib, clofarabine, cytarabine, dactinomycin, daunorubicin, doxorubicin, erlotinib, epirubicin, etoposide, fludarabine phosphate, gemcitabine, irinotecan, melphalan, methotrexate, mitomycin C, mitoxantrone, paclitaxel, sorafenib, sunitinib, temozolomide, teniposide, topotecan, vinblastine sulfate, vincristine sulfate and vinorelbine, at least 10 of the following compounds: albendazole, aprepitant, atorvastatin calcium, auraofin, celecoxib, chloroquine, cidovofir, clofazimine, clomipamine, clonidine, colchicine, digoxin, fluphenazine, fluvastatin, haloperidol, homoharringtonine, itraconazole, lovastatin, mefloquine, metformin, methylene blue, minoxidil, mycophenolate mofetil, nelfinavir, pindolol, rosuvastatin calcium, sertaline, simvastatin, sirolimus, sodium tetradecyl sulfate, trifluoperazine, valganciclovir, valproic acid and vorinostat, and disulfiram. In an embodiment, the GBM stem cell is derived from GBM tumor tissue, and the culturing comprises mechanically dissociating the GBM tissue, adding one or more dissociation enzymes to the GBM tissue, incubating the tissue to facilitate digestion of the tissue by the one or more enzymes, obtaining a suspension of cells from the digested tissue, and propagating the cells in stem cell medium to provide the culture. In an embodiment, the dissociation enzyme is ACCUTASE. In an embodiment, the incubating takes place at a temperature range between 35° C. and 39° C. In an embodiment, the incubating takes place at about 37° C. In an embodiment, the threshold level is about 50%. In an embodiment, at least one of the one or more combinations comprises at least one anti-neoplastic/chemotherapeutic compound. In an embodiment, the identifying step further comprises: from the identified two or more selected compounds, further selecting at least two compounds as preferred compounds based on at least one of the following characteristics: overall level of cell death caused in the first set of aliquots; known ability to cross the blood-brain barrier in a GBM patient; and known likely side effects to a GBM patient, and the characterizing step further comprises characterizing the GBM stem cell as suitable for treatment with one or more combinations of the preferred compounds.

In an embodiment, a combination of compounds for treating a patient having a glioblastoma multiforme (GBM) tumor wherein the compounds are selected by a method comprising surgically resecting the GBM tumor from the patient, obtaining a GBM stem cell from the surgically resected tumor, culturing the GBM stem cell to provide a culture, contacting a first set of aliquots of the culture with individual compounds selected from a panel of compounds, and identifying two or more of the selected compounds that cause more than a threshold level of cell death in the first set of aliquots, thereby identifying the compounds in the combination is disclosed.

In an embodiment, the panel comprises at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, or all, of the following compounds: AZD-7762; AZD-8055; BEZ-235; BGT-226; MG-132; NVP-AUY-922; obatoclax; PIK-75; PKI-587; staurosporine; YM155; 10-hydroxycamptothecin; anisomycin; β-peltatin; emetine; gambogic acid; mebendazole; ouabain; peruvoside; phenethyl caffeate; podophyllin acetate; pyrvinium pamoate; and thiram.

In an embodiment, the panel further comprises at least one of the following 76 compounds: albendazole, aprepitant, atorvastatin calcium, auraofin, bleomycin, bortezomib, brompheniramine maleate, captropril, carboplatin, celecoxib, chloroquine, cidovofir, cladribine, clofarabine, clofazimine, clomipamine, clonidine, colchicine, cyclophosphamide, cytarabine, dactinomycin, daunorubicin, digoxin, disulfiram, docetaxel, doxorubicin, erlotinib, ethacrynic acid, epirubicin, etoposide, fludarabine phosphate, fluorouracil, fluphenazine, fluvastatin, gemcitabine, haloperidol, homoharringtonine, hydroxychloroquine, idarubicin, irinotecan, itraconazole, ketoconazole, lomustine, lovastatin, mefloquine, melphalan, memantine, metformin, methotrexate, methylene blue, minoxidil, mitomycin C, mitoxantrone, mycophenolate mofetil, nelfinavir, nisoldipine, paclitaxel, pindolol, pitavastatin, rosuvastatin calcium, sertaline, simvastatin, sirolimus, sorafenib, sodium tetradecyl sulfate, sunitinib, temozolomide, teniposide, topotecan, trifluoperazine, valganciclovir, valproic acid, vinblastine sulfate, vincristine sulfate, vinorelbine and vorinostat. In an embodiment, the panel comprises at least 10 of the following anti-neoplastic/chemotherapeutic compounds: bortezomib, clofarabine, cytarabine, dactinomycin, daunorubicin, doxorubicin, erlotinib, epirubicin, etoposide, fludarabine phosphate, gemcitabine, irinotecan, melphalan, methotrexate, mitomycin C, mitoxantrone, paclitaxel, sorafenib, sunitinib, temozolomide, teniposide, topotecan, vinblastine sulfate, vincristine sulfate and vinorelbine, at least 10 of the following compounds: albendazole, aprepitant, atorvastatin calcium, auraofin, celecoxib, chloroquine, cidovofir, clofazimine, clomipamine, clonidine, colchicine, digoxin, fluphenazine, fluvastatin, haloperidol, homoharringtonine, itraconazole, lovastatin, mefloquine, metformin, methylene blue, minoxidil, mycophenolate mofetil, nelfinavir, pindolol, rosuvastatin calcium, sertaline, simvastatin, sirolimus, sodium tetradecyl sulfate, trifluoperazine, valganciclovir, valproic acid and vorinostat, and disulfiram. In an embodiment, the culturing comprises mechanically dissociating the GBM tissue, adding one or more dissociation enzymes to the GBM tumor, incubating the GBM tumor to facilitate digestion of the tumor by the one or more enzymes, obtaining a suspension of cells from the digested tumor, and propagating the cells in stem cell medium to provide the culture. In an embodiment, the dissociation enzyme is ACCUTASE. In an embodiment, the incubating takes place at a temperature range between 35° C. and 39° C. In an embodiment, the incubating takes place at about 37° C. In an embodiment, the threshold level is about 50%. In an embodiment, at least one of the compounds in the combination is an anti-neoplastic/chemotherapeutic compound. In an embodiment, the identifying step further comprises: from the identified two or more selected compounds, further selecting at least two compounds as preferred compounds based on at least one of the following characteristics: overall level of cell death caused in the first set of aliquots; known ability to cross the blood-brain barrier in a GBM patient; and known likely side effects to a GBM patient.

In an embodiment, a method of characterizing a glioblastoma multiforme (GBM) stem cell, comprising culturing the GBM stem cell to provide a culture, contacting a first set of aliquots of the culture with individual compounds selected from a panel of compounds, identifying two or more of the selected compounds that cause more than a threshold level of cell death in the first set of aliquots, characterizing the GBM stem cell as suitable for treatment with one or more combinations comprising the two or more identified compounds, and contacting a second set of aliquots of the culture with one or more of the combinations, identifying combinations having a synergistic effect on cell death in the second set of aliquots, and further characterizing the GBM stem cell as being suitable for treatment with thus identified synergistic combinations is disclosed.

In an embodiment, the panel comprises at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, or all, of the following compounds: AZD-7762; AZD-8055; BEZ-235; BGT-226; MG-132; NVP-AUY-922; obatoclax; PIK-75; PKI-587; staurosporine; YM155; 10-hydroxycamptothecin; anisomycin; β-peltatin; emetine; gambogic acid; mebendazole; ouabain; peruvoside; phenethyl caffeate; podophyllin acetate; pyrvinium pamoate; and thiram.

In an embodiment, the panel further comprises the following 76 compounds: albendazole, aprepitant, atorvastatin calcium, auraofin, bleomycin, bortezomib, brompheniramine maleate, captropril, carboplatin, celecoxib, chloroquine, cidovofir, cladribine, clofarabine, clofazimine, clomipamine, clonidine, colchicine, cyclophosphamide, cytarabine, dactinomycin, daunorubicin, digoxin, disulfiram, docetaxel, doxorubicin, erlotinib, ethacrynic acid, epirubicin, etoposide, fludarabine phosphate, fluorouracil, fluphenazine, fluvastatin, gemcitabine, haloperidol, homoharringtonine, hydroxychloroquine, idarubicin, irinotecan, itraconazole, ketoconazole, lomustine, lovastatin, mefloquine, melphalan, memantine, metformin, methotrexate, methylene blue, minoxidil, mitomycin C, mitoxantrone, mycophenolate mofetil, nelfinavir, nisoldipine, paclitaxel, pindolol, pitavastatin, rosuvastatin calcium, sertaline, simvastatin, sirolimus, sorafenib, sodium tetradecyl sulfate, sunitinib, temozolomide, teniposide, topotecan, trifluoperazine, valganciclovir, valproic acid, vinblastine sulfate, vincristine sulfate, vinorelbine and vorinostat. In an embodiment, the panel comprises at least 10 of the following anti-neoplastic/chemotherapeutic compounds: bortezomib, clofarabine, cytarabine, dactinomycin, daunorubicin, doxorubicin, erlotinib, epirubicin, etoposide, fludarabine phosphate, gemcitabine, irinotecan, melphalan, methotrexate, mitomycin C, mitoxantrone, paclitaxel, sorafenib, sunitinib, temozolomide, teniposide, topotecan, vinblastine sulfate, vincristine sulfate and vinorelbine, at least 10 of the following compounds: albendazole, aprepitant, atorvastatin calcium, auraofin, celecoxib, chloroquine, cidovofir, clofazimine, clomipamine, clonidine, colchicine, digoxin, fluphenazine, fluvastatin, haloperidol, homoharringtonine, itraconazole, lovastatin, mefloquine, metformin, methylene blue, minoxidil, mycophenolate mofetil, nelfinavir, pindolol, rosuvastatin calcium, sertaline, simvastatin, sirolimus, sodium tetradecyl sulfate, trifluoperazine, valganciclovir, valproic acid and vorinostat, and disulfiram. In an embodiment, the GBM stem cell is derived from GBM tumor tissue, and the culturing comprises mechanically dissociating the GBM tissue, adding a combination of dissociation enzymes to the GBM tissue, incubating the tissue to facilitate digestion of the tissue by the enzyme, obtaining a suspension of cells from the digested tissue, and propagating the cells in stem cell medium to provide the culture. In an embodiment, the dissociation enzyme is ACCUTASE. In an embodiment, the incubating takes place at a temperature range between 35° C. and 39° C. In an embodiment, the incubating takes place at about 37° C. In an embodiment, the threshold level is about 50%. In an embodiment, at least one of the one or more combinations comprises at least one anti-neoplastic/chemotherapeutic compound. In an embodiment, the identifying step further comprises: from the identified two or more selected compounds, further selecting at least two compounds as preferred compounds based on at least one of the following characteristics: overall level of cell death caused in the first set of aliquots; known ability to cross the blood-brain barrier in a GBM patient; and known likely side effects to a GBM patient.

In an embodiment, a method of characterizing a glioblastoma multiforme (GBM) stem cell, comprising culturing the GBM stem cell to provide a culture, contacting a first set of aliquots of the culture with individual compounds selected from a panel of compounds comprising In an embodiment, the panel comprises at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, or all, of the following compounds: AZD-7762; AZD-8055; BEZ-235; BGT-226; MG-132; NVP-AUY-922; obatoclax; PIK-75; PKI-587; staurosporine; YM155; 10-hydroxycamptothecin; anisomycin; β-peltatin; emetine; gambogic acid; mebendazole; ouabain; peruvoside; phenethyl caffeate; podophyllin acetate; pyrvinium pamoate; and thiram, and optionally comprising at least one of the following 76 compounds: albendazole, aprepitant, atorvastatin calcium, auraofin, bleomycin, bortezomib, brompheniramine maleate, captropril, carboplatin, celecoxib, chloroquine, cidovofir, cladribine, clofarabine, clofazimine, clomipamine, clonidine, colchicine, cyclophosphamide, cytarabine, dactinomycin, daunorubicin, digoxin, disulfiram, docetaxel, doxorubicin, erlotinib, ethacrynic acid, epirubicin, etoposide, fludarabine phosphate, fluorouracil, fluphenazine, fluvastatin, gemcitabine, haloperidol, homoharringtonine, hydroxychloroquine, idarubicin, irinotecan, itraconazole, ketoconazole, lomustine, lovastatin, mefloquine, melphalan, memantine, metformin, methotrexate, methylene blue, minoxidil, mitomycin C, mitoxantrone, mycophenolate mofetil, nelfinavir, nisoldipine, paclitaxel, pindolol, pitavastatin, rosuvastatin calcium, sertaline, simvastatin, sirolimus, sorafenib, sodium tetradecyl sulfate, sunitinib, temozolomide, teniposide, topotecan, trifluoperazine, valganciclovir, valproic acid, vinblastine sulfate, vincristine sulfate, vinorelbine and vorinostat, identifying two or more of the selected compounds that cause more than a threshold level of cell death in the first set of aliquots, characterizing the GBM stem cell as suitable for treatment with one or more combinations comprising the two or more identified compounds, and contacting a second set of aliquots of the culture with one or more of the combinations, identifying combinations having a synergistic effect on cell death in the second set of aliquots, and further characterizing the GBM stem cell as being suitable for treatment with thus identified synergistic combinations is disclosed.

In an embodiment, the GBM stem cell is derived from GBM tumor tissue, and the culturing comprises mechanically dissociating the GBM tissue, adding a combination of dissociation enzymes to the GBM tissue, incubating the tissue to facilitate digestion of the tissue by the enzyme, obtaining a suspension of cells from the digested tissue, and propagating the cells in stem cell medium to provide the culture. In an embodiment, the dissociation enzyme is ACCUTASE. In an embodiment, the incubating takes place at a temperature range between 35° C. and 39° C. In an embodiment, the incubating takes place at about 37° C. In an embodiment, the threshold level is about 50%. In an embodiment, at least one of the one or more combinations comprises at least one anti-neoplastic/chemotherapeutic compound. In an embodiment, the identifying step further comprises: from the identified two or more selected compounds, further selecting at least two compounds as preferred compounds based on at least one of the following characteristics: overall level of cell death caused in the first set of aliquots; known ability to cross the blood-brain barrier in a GBM patient; and known likely side effects to a GBM patient.

In an embodiment, a method of characterizing a glioblastoma multiforme (GBM) tumor comprising surgically resecting the GBM tumor from the patient, obtaining a GBM stem cell from the surgically resected tumor, culturing the GBM stem cell to provide a culture, contacting a first set of aliquots of the culture with individual compounds selected from a panel of compounds, identifying two or more of the selected compounds that cause more than a threshold level of cell death in the first set of aliquots, and characterizing the GBM tumor as suitable for treatment with one or more combinations of the two or more identified compounds is disclosed.

In an embodiment, the panel comprises at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, or all, of the following compounds: AZD-7762; AZD-8055; BEZ-235; BGT-226; MG-132; NVP-AUY-922; obatoclax; PIK-75; PKI-587; staurosporine; YM155; 10-hydroxycamptothecin; anisomycin; β-peltatin; emetine; gambogic acid; mebendazole; ouabain; peruvoside; phenethyl caffeate; podophyllin acetate; pyrvinium pamoate; and thiram.

In an embodiment, the panel further comprises at least one of the following 76 compounds: albendazole, aprepitant, atorvastatin calcium, auraofin, bleomycin, bortezomib, brompheniramine maleate, captropril, carboplatin, celecoxib, chloroquine, cidovofir, cladribine, clofarabine, clofazimine, clomipamine, clonidine, colchicine, cyclophosphamide, cytarabine, dactinomycin, daunorubicin, digoxin, disulfiram, docetaxel, doxorubicin, erlotinib, ethacrynic acid, epirubicin, etoposide, fludarabine phosphate, fluorouracil, fluphenazine, fluvastatin, gemcitabine, haloperidol, homoharringtonine, hydroxychloroquine, idarubicin, irinotecan, itraconazole, ketoconazole, lomustine, lovastatin, mefloquine, melphalan, memantine, metformin, methotrexate, methylene blue, minoxidil, mitomycin C, mitoxantrone, mycophenolate mofetil, nelfinavir, nisoldipine, paclitaxel, pindolol, pitavastatin, rosuvastatin calcium, sertaline, simvastatin, sirolimus, sorafenib, sodium tetradecyl sulfate, sunitinib, temozolomide, teniposide, topotecan, trifluoperazine, valganciclovir, valproic acid, vinblastine sulfate, vincristine sulfate, vinorelbine and vorinostat. In an embodiment, the panel comprises at least 10 of the following anti-neoplastic/chemotherapeutic compounds: bortezomib, clofarabine, cytarabine, dactinomycin, daunorubicin, doxorubicin, erlotinib, epirubicin, etoposide, fludarabine phosphate, gemcitabine, irinotecan, melphalan, methotrexate, mitomycin C, mitoxantrone, paclitaxel, sorafenib, sunitinib, temozolomide, teniposide, topotecan, vinblastine sulfate, vincristine sulfate and vinorelbine, at least 10 of the following compounds: albendazole, aprepitant, atorvastatin calcium, auraofin, celecoxib, chloroquine, cidovofir, clofazimine, clomipamine, clonidine, colchicine, digoxin, fluphenazine, fluvastatin, haloperidol, homoharringtonine, itraconazole, lovastatin, mefloquine, metformin, methylene blue, minoxidil, mycophenolate mofetil, nelfinavir, pindolol, rosuvastatin calcium, sertaline, simvastatin, sirolimus, sodium tetradecyl sulfate, trifluoperazine, valganciclovir, valproic acid and vorinostat, and disulfiram. In an embodiment, the culturing comprises mechanically dissociating the GBM tissue, adding a combination of dissociation enzymes to the GBM tumor, incubating the GBM tumor to facilitate digestion of the tumor by the enzyme, obtaining a suspension of cells from the digested tumor, and propagating the cells in stem cell medium to provide the culture. In an embodiment, the dissociation enzyme is ACCUTASE. In an embodiment, the incubating takes place at a temperature range between 35° C. and 39° C. In an embodiment, the incubating takes place at about 37° C. In an embodiment, the threshold level is about 50%. In an embodiment, at least one of the compounds in the combination is an anti-neoplastic/chemotherapeutic compound. In an embodiment, the identifying step further comprises: from the identified two or more selected compounds, further selecting at least two compounds as preferred compounds based on at least one of the following characteristics: overall level of cell death caused in the first set of aliquots; known ability to cross the blood-brain barrier in a GBM patient; and known likely side effects to a GBM patient, and the characterizing step further comprises characterizing the GBM tumor as suitable for treatment with one or more combinations of the preferred compounds.

In an embodiment, a method of killing or inhibiting growth of a glioblastoma multiforme (GBM) tumor in a patient, comprising surgically resecting the GBM tumor from the patient, obtaining a GBM stem cell from the surgically resected tumor, culturing the GBM stem cell to provide a culture, contacting a first set of aliquots of the culture with individual compounds selected from a panel of compounds, identifying two or more of the selected compounds that cause more than a threshold level of cell death in the first set of aliquots, and treating the patient with one or more combinations of the two or more identified compounds is disclosed.

In an embodiment, the panel comprises at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, or all, of the following compounds: AZD-7762; AZD-8055; BEZ-235; BGT-226; MG-132; NVP-AUY-922; obatoclax; PIK-75; PKI-587; staurosporine; YM155; 10-hydroxycamptothecin; anisomycin; β-peltatin; emetine; gambogic acid; mebendazole; ouabain; peruvoside; phenethyl caffeate; podophyllin acetate; pyrvinium pamoate; and thiram.

In an embodiment, the panel further comprises at least one of the following 76 compounds: albendazole, aprepitant, atorvastatin calcium, auraofin, bleomycin, bortezomib, brompheniramine maleate, captropril, carboplatin, celecoxib, chloroquine, cidovofir, cladribine, clofarabine, clofazimine, clomipamine, clonidine, colchicine, cyclophosphamide, cytarabine, dactinomycin, daunorubicin, digoxin, disulfiram, docetaxel, doxorubicin, erlotinib, ethacrynic acid, epirubicin, etoposide, fludarabine phosphate, fluorouracil, fluphenazine, fluvastatin, gemcitabine, haloperidol, homoharringtonine, hydroxychloroquine, idarubicin, irinotecan, itraconazole, ketoconazole, lomustine, lovastatin, mefloquine, melphalan, memantine, metformin, methotrexate, methylene blue, minoxidil, mitomycin C, mitoxantrone, mycophenolate mofetil, nelfinavir, nisoldipine, paclitaxel, pindolol, pitavastatin, rosuvastatin calcium, sertaline, simvastatin, sirolimus, sorafenib, sodium tetradecyl sulfate, sunitinib, temozolomide, teniposide, topotecan, trifluoperazine, valganciclovir, valproic acid, vinblastine sulfate, vincristine sulfate, vinorelbine and vorinostat. In an embodiment, the panel comprises at least 10 of the following anti-neoplastic/chemotherapeutic compounds: bortezomib, clofarabine, cytarabine, dactinomycin, daunorubicin, doxorubicin, erlotinib, epirubicin, etoposide, fludarabine phosphate, gemcitabine, irinotecan, melphalan, methotrexate, mitomycin C, mitoxantrone, paclitaxel, sorafenib, sunitinib, temozolomide, teniposide, topotecan, vinblastine sulfate, vincristine sulfate and vinorelbine, at least 10 of the following compounds: albendazole, aprepitant, atorvastatin calcium, auraofin, celecoxib, chloroquine, cidovofir, clofazimine, clomipamine, clonidine, colchicine, digoxin, fluphenazine, fluvastatin, haloperidol, homoharringtonine, itraconazole, lovastatin, mefloquine, metformin, methylene blue, minoxidil, mycophenolate mofetil, nelfinavir, pindolol, rosuvastatin calcium, sertaline, simvastatin, sirolimus, sodium tetradecyl sulfate, trifluoperazine, valganciclovir, valproic acid and vorinostat, and disulfiram. In an embodiment, the culturing comprises mechanically dissociating the GBM tissue, adding a combination of dissociation enzymes to the GBM tumor, incubating the GBM tumor to facilitate digestion of the tumor by the enzyme, obtaining a suspension of cells from the digested tumor, and propagating the cells in stem cell medium to provide the culture. In an embodiment, the dissociation enzyme is ACCUTASE. In an embodiment, the incubating takes place at a temperature range between 35° C. and 39° C. In an embodiment, the incubating takes place at about 37° C. In an embodiment, the threshold level is about 50%. In an embodiment, at least one of the one or more combinations comprises at least one anti-neoplastic/chemotherapeutic compound. In an embodiment, the identifying step further comprises: from the identified two or more selected compounds, further selecting at least two compounds as preferred compounds based on at least one of the following characteristics: overall level of cell death caused in the first set of aliquots; known ability to cross the blood-brain barrier in a GBM patient; and known likely side effects to a GBM patient.

In an embodiment, a method of treating a patient having a glioblastoma multiforme (GBM) tumor, comprising surgically resecting the GBM tumor from the patient, obtaining a GBM stem cell from the surgically resected tumor, culturing the GBM stem cell to provide a culture, contacting a first set of aliquots of the culture with individual compounds selected from a panel of compounds, identifying two or more of the selected compounds that cause more than a threshold level of cell death in the first set of aliquots, and treating the patient with one or more combinations of the two or more identified compounds is disclosed.

In an embodiment, the panel comprises at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, or all, of the following compounds: AZD-7762; AZD-8055; BEZ-235; BGT-226; MG-132; NVP-AUY-922; obatoclax; PIK-75; PKI-587; staurosporine; YM155; 10-hydroxycamptothecin; anisomycin; β-peltatin; emetine; gambogic acid; mebendazole; ouabain; peruvoside; phenethyl caffeate; podophyllin acetate; pyrvinium pamoate; and thiram.

In an embodiment, the panel further comprises at least one of the following 76 compounds: albendazole, aprepitant, atorvastatin calcium, auraofin, bleomycin, bortezomib, brompheniramine maleate, captropril, carboplatin, celecoxib, chloroquine, cidovofir, cladribine, clofarabine, clofazimine, clomipamine, clonidine, colchicine, cyclophosphamide, cytarabine, dactinomycin, daunorubicin, digoxin, disulfiram, docetaxel, doxorubicin, erlotinib, ethacrynic acid, epirubicin, etoposide, fludarabine phosphate, fluorouracil, fluphenazine, fluvastatin, gemcitabine, haloperidol, homoharringtonine, hydroxychloroquine, idarubicin, irinotecan, itraconazole, ketoconazole, lomustine, lovastatin, mefloquine, melphalan, memantine, metformin, methotrexate, methylene blue, minoxidil, mitomycin C, mitoxantrone, mycophenolate mofetil, nelfinavir, nisoldipine, paclitaxel, pindolol, pitavastatin, rosuvastatin calcium, sertaline, simvastatin, sirolimus, sorafenib, sodium tetradecyl sulfate, sunitinib, temozolomide, teniposide, topotecan, trifluoperazine, valganciclovir, valproic acid, vinblastine sulfate, vincristine sulfate, vinorelbine and vorinostat. In an embodiment, the panel comprises at least 10 of the following anti-neoplastic/chemotherapeutic compounds: bortezomib, clofarabine, cytarabine, dactinomycin, daunorubicin, doxorubicin, erlotinib, epirubicin, etoposide, fludarabine phosphate, gemcitabine, irinotecan, melphalan, methotrexate, mitomycin C, mitoxantrone, paclitaxel, sorafenib, sunitinib, temozolomide, teniposide, topotecan, vinblastine sulfate, vincristine sulfate and vinorelbine, at least 10 of the following compounds: albendazole, aprepitant, atorvastatin calcium, auraofin, celecoxib, chloroquine, cidovofir, clofazimine, clomipamine, clonidine, colchicine, digoxin, fluphenazine, fluvastatin, haloperidol, homoharringtonine, itraconazole, lovastatin, mefloquine, metformin, methylene blue, minoxidil, mycophenolate mofetil, nelfinavir, pindolol, rosuvastatin calcium, sertaline, simvastatin, sirolimus, sodium tetradecyl sulfate, trifluoperazine, valganciclovir, valproic acid and vorinostat, and disulfiram. In an embodiment, the culturing comprises mechanically dissociating the GBM tissue, adding a combination of dissociation enzymes to the GBM tumor, incubating the GBM tumor to facilitate digestion of the tumor by the enzyme, obtaining a suspension of cells from the digested tumor, and propagating the cells in stem cell medium to provide the culture. In an embodiment, the dissociation enzyme is ACCUTASE. In an embodiment, the incubating takes place at a temperature range between 35° C. and 39° C. In an embodiment, the incubating takes place at about 37° C. In an embodiment, the threshold level is about 50%. In an embodiment, at least one of the one or more combinations comprises at least one anti-neoplastic/chemotherapeutic compound. In an embodiment, the identifying step further comprises: from the identified two or more selected compounds, further selecting at least two compounds as preferred compounds based on at least one of the following characteristics: overall level of cell death caused in the first set of aliquots; known ability to cross the blood-brain barrier in a GBM patient; and known likely side effects to a GBM patient.

In an embodiment, a method of characterizing a glioblastoma multiforme (GBM) stem cell from surgically resected primary GBM tissue comprising culturing the GBM stem cell to provide a culture by mechanically dissociating the GBM tissue, adding a combination of dissociation enzymes to the GBM tissue, incubating the tissue to facilitate digestion of the tissue by the enzyme, obtaining a suspension of cells from the digested tissue, and propagating the cells in stem cell medium to provide the culture, followed by contacting a first set of aliquots of the culture with a plurality of concentrations of individual compounds selected from a panel of compounds, identifying two or more compounds from the panel demonstrating more than 50% cell death, contacting a second set of aliquots of the culture with one or more combinations of the identified two or more compounds, and identifying among the combinations those having a synergistic effect on cell death in the second set of aliquots, and further characterizing the GBM stem cell as being susceptible to treatment by thus identified synergistic combinations is disclosed.

In an embodiment, a panel of compounds for use in characterizing the sensitivity of a cancer cell to one or more combinations of the compounds comprising at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, or all, of the following compounds AZD-7762; AZD-8055; BEZ-235; BGT-226; MG-132; NVP-AUY-922; obatoclax; PIK-75; PKI-587; staurosporine; YM155; 10-hydroxycamptothecin; anisomycin; β-peltatin; emetine; gambogic acid; mebendazole; ouabain; peruvoside; phenethyl caffeate; podophyllin acetate; pyrvinium pamoate; and thiram.

In an embodiment, the panel further comprises at least one of the following compounds: albendazole, aprepitant, atorvastatin calcium, auraofin, bleomycin, bortezomib, brompheniramine maleate, captropril, carboplatin, celecoxib, chloroquine, cidovofir, cladribine, clofarabine, clofazimine, clomipamine, clonidine, colchicine, cyclophosphamide, cytarabine, dactinomycin, daunorubicin, digoxin, disulfiram, docetaxel, doxorubicin, erlotinib, ethacrynic acid, epirubicin, etoposide, fludarabine phosphate, fluorouracil, fluphenazine, fluvastatin, gemcitabine, haloperidol, homoharringtonine, hydroxychloroquine, idarubicin, irinotecan, itraconazole, ketoconazole, lomustine, lovastatin, mefloquine, melphalan, memantine, metformin, methotrexate, methylene blue, minoxidil, mitomycin C, mitoxantrone, mycophenolate mofetil, nelfinavir, nisoldipine, paclitaxel, pindolol, pitavastatin, rosuvastatin calcium, sertaline, simvastatin, sirolimus, sorafenib, sodium tetradecyl sulfate, sunitinib, temozolomide, teniposide, topotecan, trifluoperazine, valganciclovir, valproic acid, vinblastine sulfate, vincristine sulfate, vinorelbine and vorinostat.

In an embodiment, a method of determining the suitability of a glioblastoma multiforme (GBM) patient for treatment with one or more combinations of two or more compounds selected from a panel, the method comprising obtaining a GBM stem cell from the patient, culturing the GBM stem cell to provide a culture, contacting a first set of aliquots of the culture with individual compounds selected from the panel, identifying two or more of the selected compounds that cause more than a threshold level of cell death in the first set of aliquots, and characterizing the patient as suitable for treatment with one or more combinations of the identified two or more compounds is disclosed.

In an embodiment, the culture comprises at least 20,000 GBM stem cells per mL to be tested. In an embodiment, the aliquots comprise at least 1000 GBM stem cells per aliquot. In an embodiment, the aliquots are contacted with a plurality of concentrations of a tested compound to provide a dose response curve for the tested compound. In an embodiment, the level of cell death is determined using a luciferase assay.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
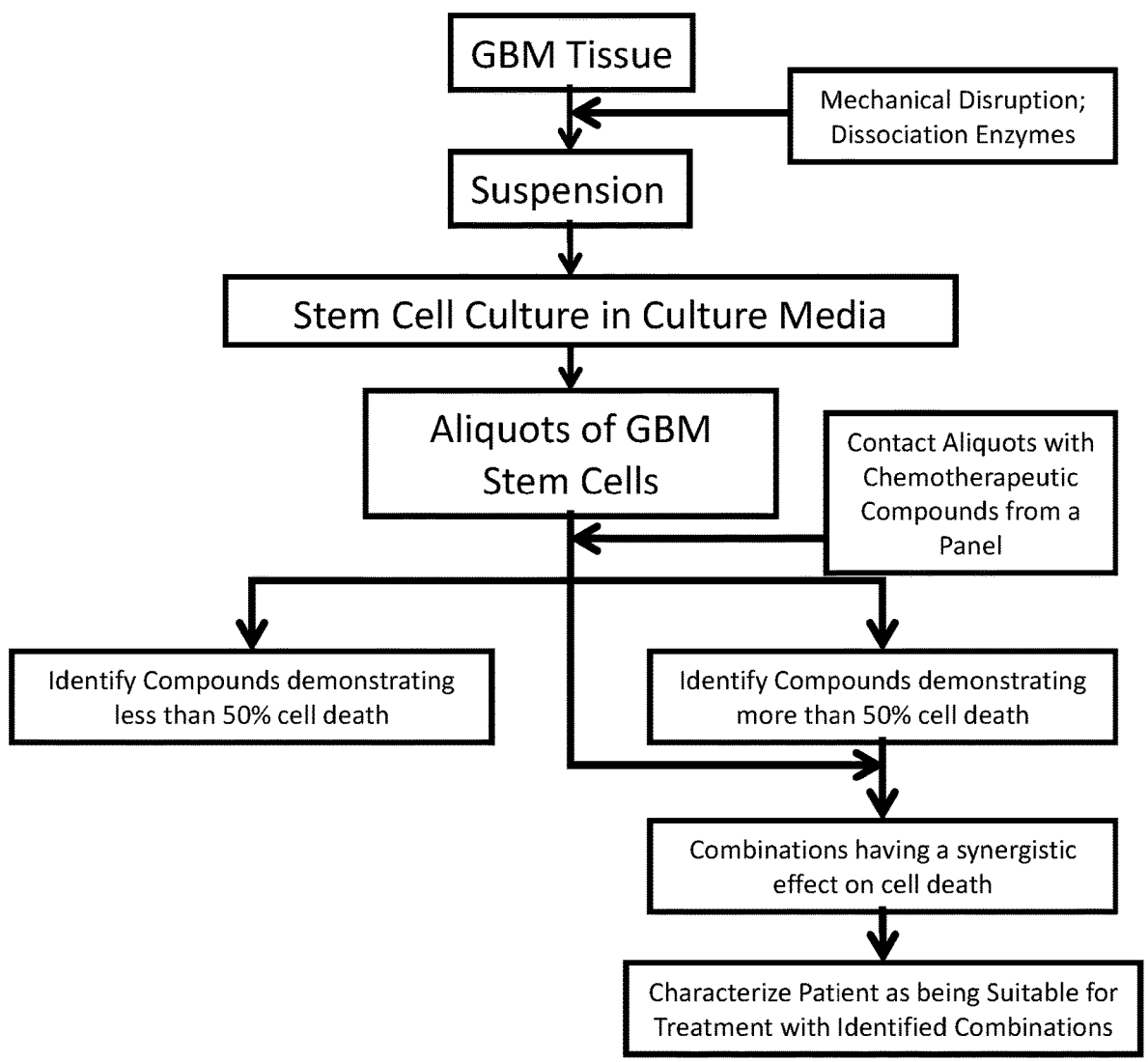
FIG. 1 is a flow chart showing steps of a method of identifying a combination of compounds causing a high level of GBM stem cell death, and of characterizing such GBM stem cells as suitable for treatment with the identified combination of compounds, according to an embodiment of the methods disclosed and described herein.
Figure 2:
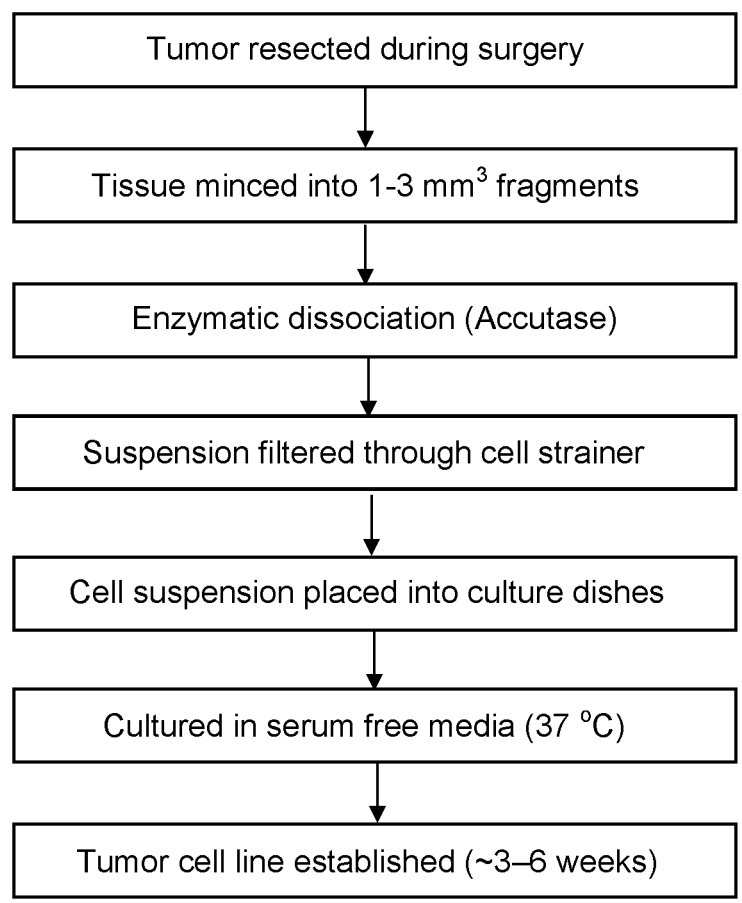
FIG. 2 is a flow chart showing a procedure for establishing tumor-derived cultures from tissue specimens, according to an embodiment of methods disclosed and described herein.
Figure 3:
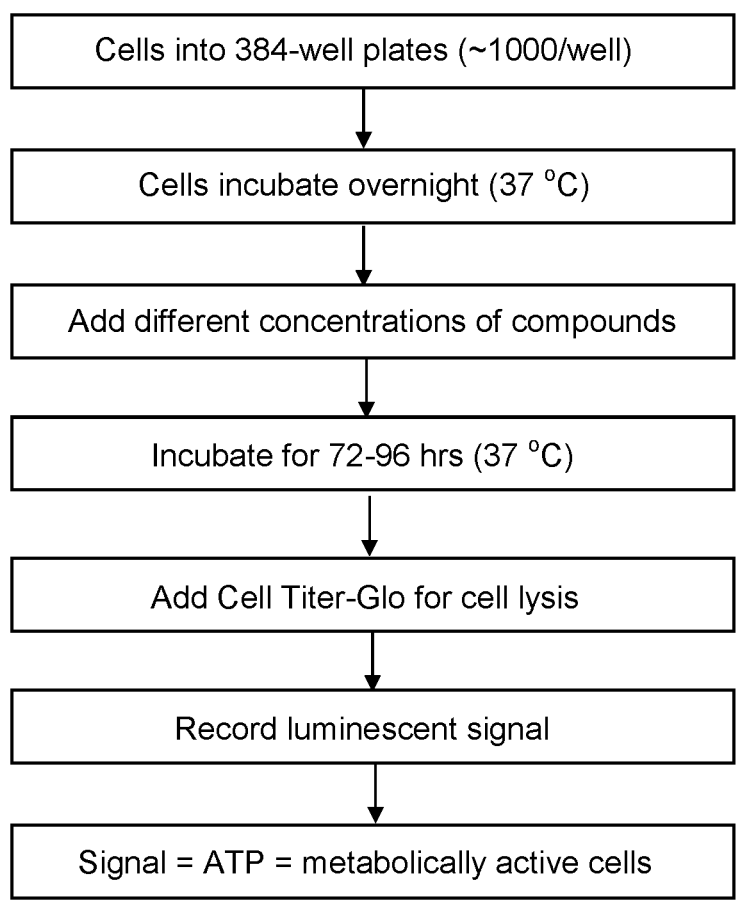
FIG. 3 is a flow chart showing a summary of high-throughput screening (HTS) methodology, according to an embodiment of methods disclosed and described herein.
Figure 4:
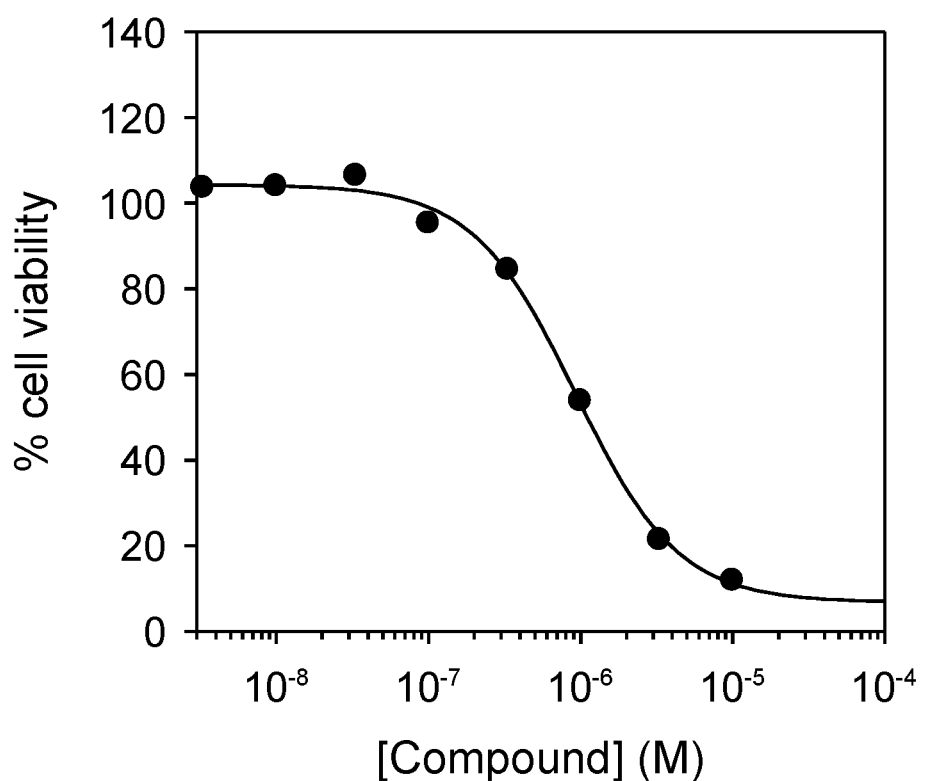
FIG. 4 is an example of a typical dose response curve generated by performing high-throughput screening (HTS) assays of methods disclosed and described herein, for example, the HTS method exemplified in FIG. 3. Dose response curves are used to determine IC50 for compounds and drugs.
Figure 5:
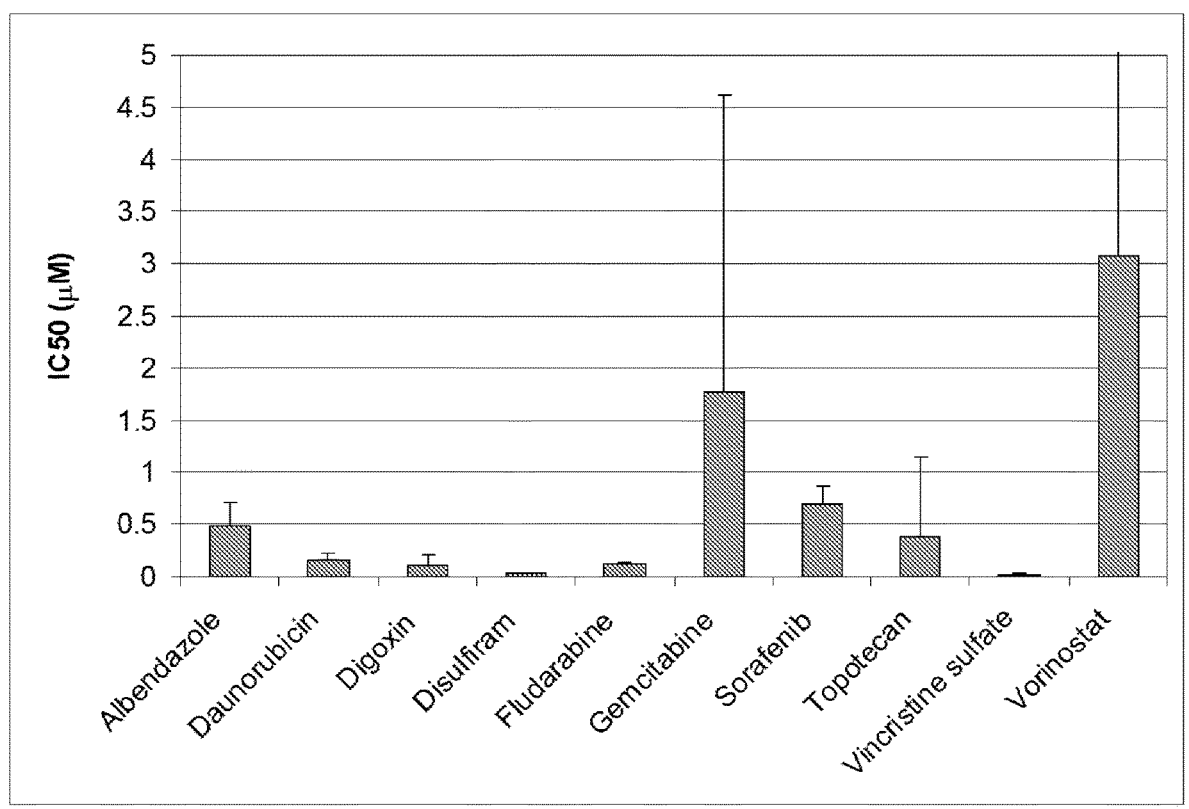
FIG. 5 is a graph of IC50 values determined for individual compounds from dose response curves corresponding to the average IC50 (n=at least 3) determined from high-throughput screening (HTS) assays with patient-derived GBM stem cells.
Figure 6:
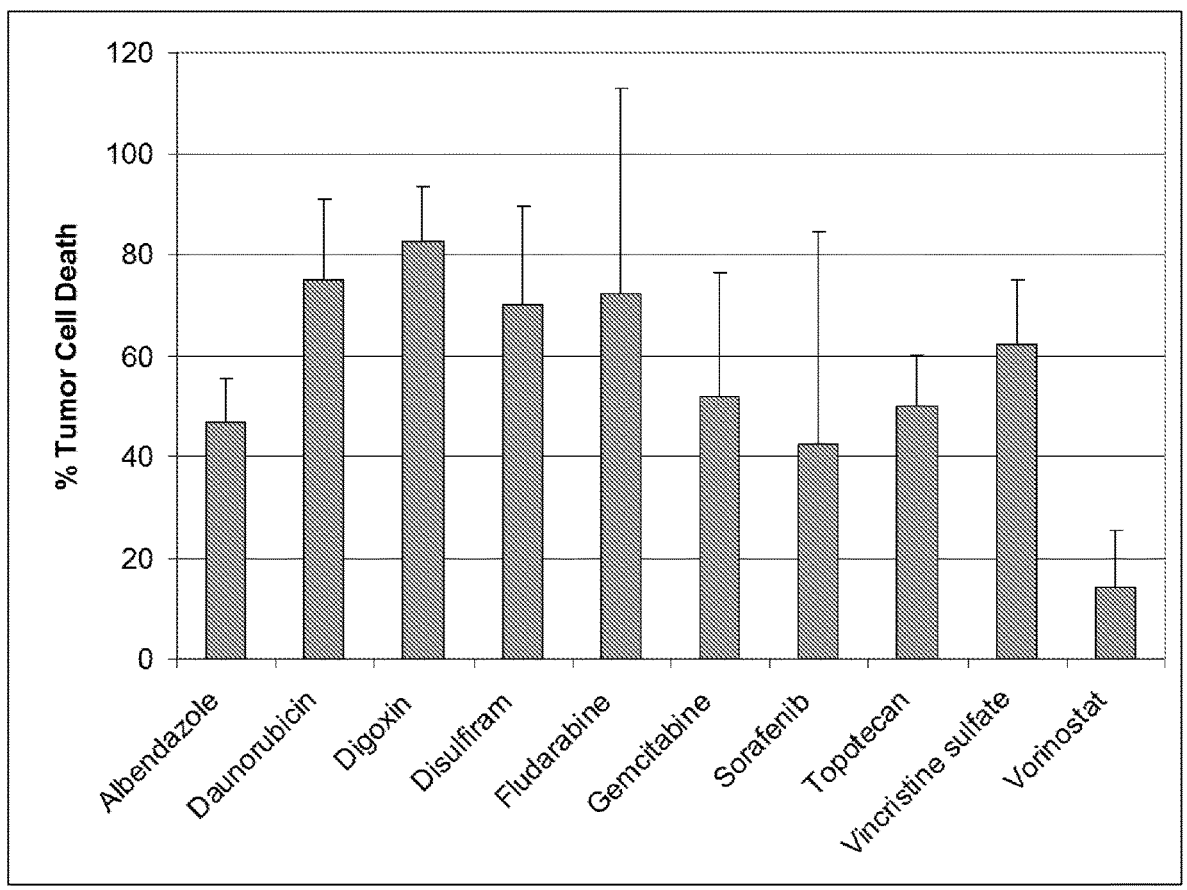
FIG. 6 is a graph of the percentage tumor cell death determined for individual compounds. Data correspond to average tumor cell death (n=5) observed at 1 μM drug concentration.
Figure 7:
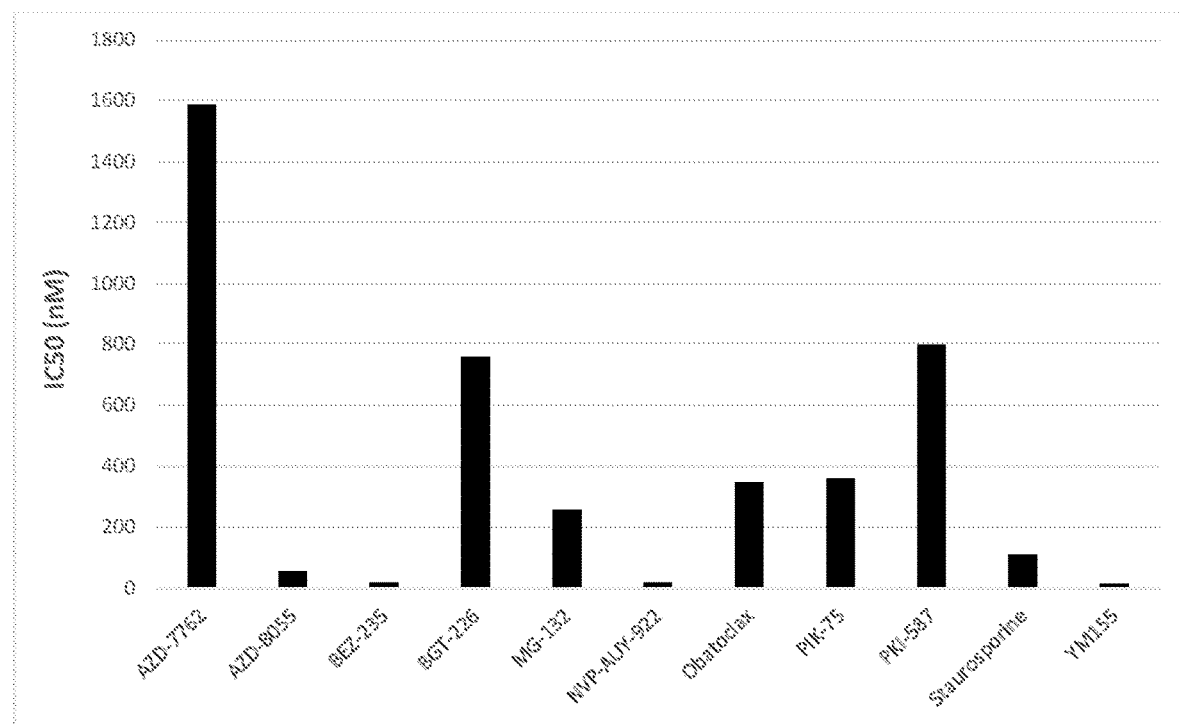
FIG. 7 is a graph of IC50 values determined for individual compounds from dose response curves corresponding to the average IC50 (n=at least 5) determined from high-throughput screening (HTS) assays with patient-derived GBM stem cells.
Figure 8:
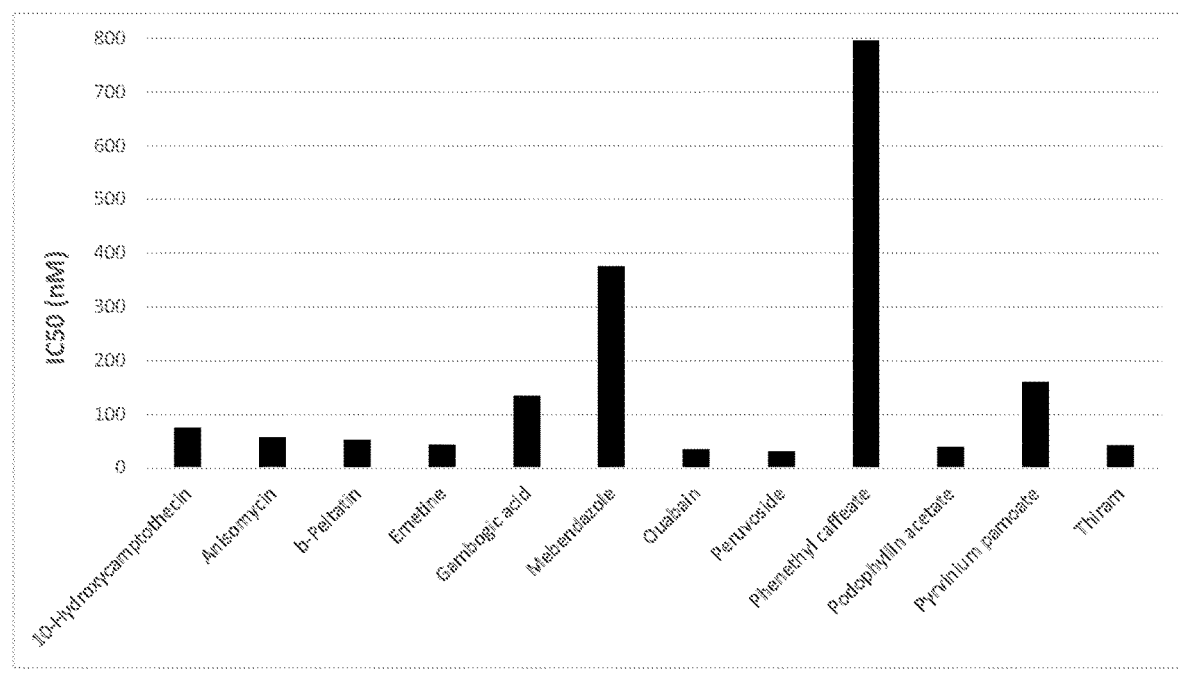
FIG. 8 is a graph of IC50 values determined for individual compounds from dose response curves corresponding to the average $IC_{50}$ (n=at least 5) determined from high-throughput screening (HTS) assays with patient-derived GBM stem cells.

A "subject", "individual", or "patient" of which characterization, and to which administration, is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., rodents (e.g., mice, rats, guinea pigs, hamsters), primates (e.g., cynomolgus monkeys, rhesus monkeys); commercially-relevant mammals such as cattle, pigs, horses, sheep, goats, cats, and/or dogs) and birds (e.g., commercially relevant birds such as chickens, ducks, geese, and/or turkeys). The animal may be a male or female at any stage of development. A non-human animal may be a transgenic animal.

As used herein, the terms "treatment," "treat," and "treating" refer to reversing, alleviating, delaying the onset of, or inhibiting the progress of a disease, disorder, or condition, or one or more signs or symptoms thereof described herein, or, in some cases, to killing or inhibiting growth of cancer stem cells in culture in order to characterize such cells' response to administration of (a) given chemotherapeutic agent(s), thereby providing information as to the suitability of the patient from whom such cells are derived for treatment with such agent(s). In some embodiments, treatment may be administered after one or more signs or symptoms have developed or been observed. In other embodiments, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

An "effective amount" of the described composition or combination refers to an amount sufficient to elicit a biological response, i.e., treating the condition. As will be appreciated by those of ordinary skill in the art, the effective amount may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of the composition or combination may reduce the tumor burden or stop the growth or spread of a tumor by eliminating cancerous cells.

In certain embodiments, an effective amount of a chemotherapeutic for administration to a 70 kg adult human may comprise about 1 mg/m$^2$ to about 500 mg/m$^2$, about 10 mg/m$^2$ to about 400 mg/m$^2$, about 50 mg/m$^2$ to about 300 mg/m$^2$, about 100 mg/m$^2$ to about 300 mg/m$^2$, about 150 mg/m$^2$ to about 250 mg/m$^2$, or about 200 mg/m$^2$ to about 250 mg/m$^2$ of the patient's body surface area of a compound per unit dosage form. In certain embodiments, an effect amount of a compound for administration is determined according to standard appropriate dosages known to practitioners.

As used herein, the terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplascm arm" is generally well differentiated, has characteristically slower growth than a malignant neoplasm, and remains localized to the site of origin. In addition, a benign neoplasm does not have the capacity to infiltrate, invade, or metastasize to distant sites. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or secondary cell mass" of the tissue type of the primary or original tumor and not of that of the organ or tissue in which the secondary (metastatic) tumor is located. For example, a breast cancer that has migrated to the lungs is said to be metastasized breast cancer and includes cancerous breast cancer cells growing in lung tissue. In the case of glioblastomas, which are the most aggressive primary brain tumors in humans, the tumor cells migrate within the brain and these migrating cells eventually develop recurrent tumors soon after the seeming eradication of the primary tumor.

As used herein, the term "cancer" refers to a malignant neoplasm (*Stedman's Medical Dictionary*, 25$^{th}$ ed.; Hensyl ed.; Williams & Wilkins: Philadelphia, 1990). An exemplary cancer is, but is not limited to, brain cancer (including, without limitation, meningioma, glioblastomas including glioblastoma multiforme, glioma (e.g., astrocytoma, oligodendroglioma), medulloblastoma).

As used herein, the term "surgical resection" refers to a surgical procedure to remove part of an organ or structure, such as a mass of tumor cells. A craniotomy is typically indicated for brain tumors so that the tumor can be removed and/or reduced in size. Resection can be performed via a resecting device, such as a cutting device or a suction device. As used herein, the term "focal radiation" refers to treatment using external beams, such as photon or proton beams. Focal radiation can be delivered via advanced radiosurgery delivery methods such as GAMMA KNIFE (Elekta, Stockholm, Sweden), CYBERKNIFE (Accuray Inc., Sunnyvale, Calif.), and the TRILOGY SYSTEM (Varian, Palo Alto, Calif.).

As used herein, "culture" or "cell culture" refers to the maintenance of cells in an artificial (e.g., an in vitro) environment. It is to be understood that the term "cell culture" is a generic term and includes include single cell suspensions, tissue culture, organ culture, and the like. "Propagation" refers to the maintenance of cells in an artificial environment under conditions favoring growth, differentiation, or continued viability, in an active or quiescent state. A cell culture may be subdivided into aliquots—each aliquot being a portion of the total volume of the original cell culture.

As used herein, the terms "chemotherapeutic agent" or "chemotherapeutic compound" refer to a chemical or chemicals known or suspected to be useful in the treatment of cancer. Examples of chemotherapeutic agents include alkylating antineoplastic agents, anti-metabolites, anti-microtubule agents, topoisomerase inhibitors, and cytotoxic antibiotics. As used herein, the term "antineoplastic" means inhibiting or preventing the growth of cancer, e.g., reducing the growth of cancer relative to the absence of a given therapy or treatment.

As used herein, "synergistic" refers to an effect achieved with a combination of compounds that is greater than the sum of the effects achieved with each component alone, also referred to as an "additive effect." As used herein, "administering" refers to administration of one or more compounds to the same patient. Administration may be done in any manner known in the art, including oral, parenteral, and intravenous administration of a compound.

"Disulfiram," (IUPAC name: 1,1',1",1"'-[disulfanediylbis (carbonothioylnitriolo)] tetraethane), is a drug used to support the treatment of chronic alcoholism. Disulfiram has the following formula:

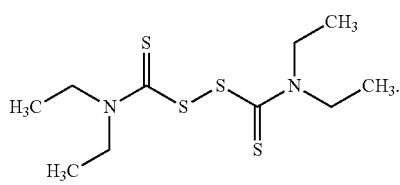 [SMILES: CCN(CC)C(=S)SSC(=S)N(CC)CC]

Disulfiram blocks the processing of alcohol in the body by inhibiting acetaldehyde dehydrogenase.

As used herein the following chemical names correspond with the following Chemical Abstracts Service (CAS) identifier numbers:

| Compound Name Used Herein | Corresponding Chemical Abstracts Service (CAS) identifier number |
|---|---|
| AZD-7762 | 860352-01-8 |
| AZD-8055 | 1009298-09-2 |
| BEZ-235 | 915019-65-7 |
| BGT-226 | 1245537-68-1 |
| MG-132 | 133407-82-6 |
| NVP-AUY-922 | 747412-49-3 |
| PIK-75 | 372196-77-5 |
| PKI-587 | 1197160-78-3 |
| YM155 | 781661-94-7 |

As used herein, the term "cancer stem cell" refers to undifferentiated cells with the ability to self-renew, differentiate to multiple lineages, and initiate tumors that resemble the parent tumor. Cancer stem cells are uniquely able to initiate and sustain the disease.

Glioblastoma multiforme (GBM) is associated with one of the worst 5-year survival rates of all human cancers, with an average survival time after diagnosis of only 12-14 months. Long-term survivors (defined as patients that survive for more than 36 months) represent only 3-5% of the total patient population (Krex et al., BRAIN 130(10):2596-2606 (2007)).

The current standard primary therapy of GBM includes surgical resection of the tumor mass followed by radiation in the vicinity of the resection cavity (usually 1-2 cm) and administration of a chemotherapeutic agent, such as temozolomide (Stupp et al., THE NEW ENGLAND JOURNAL OF MEDICINE 352(10):987-96 (2005); Stupp et al., ONKOLOGIE 28(6-7):315-7 (2005)). Even with this multi-therapeutic approach, tumor recurrence is inevitable in the majority of cases (Wick et al., NEURO-ONCOLOGY 13(6):566-79 (2011)). This is partly due to the migration properties of the tumor cells, which invade the brain parenchyma creating multiple finger-like projections within the brain that make their physical elimination virtually impossible (Friedl et al., NATURE REVIEWS CANCER 3(5):362-74 (2003)). These projections often contain a sub-population of cancer stem cells or tumor-initiating cells that persist after primary therapy and give rise to recurrent tumors.

The low GBM survival rate is thought to be partly due to difficulty eradicating cancer stem cells, which are undifferentiated cells with the ability to self-renew, differentiate to multiple lineages, and initiate tumors that resemble the parent tumor (Binello et al., CANCER SCIENCE 102(11):1958-1966 (2011)). In GBM, targeting cancer stem cells as the potential cause of tumor recurrence clearly represents an opportunity to improve patient prognosis. In particular, targeting GBM cancer stem cells (GSCs) with one or more specific chemotherapeutic agents that effectively kill or inhibit growth of GSCs represents such an opportunity.

It has been surprisingly observed that GSCs derived from different individual GBM subjects respond differently to administration of different chemical agents or compounds, which may or may not be known or suspected chemotherapeutic. For example, it has been observed that aliquots of GSC cultures derived from certain individual subjects demonstrate relatively high levels of cell death when those aliquots are contacted with a given chemical agents or compounds, whereas such aliquots from other individual subjects demonstrate relatively low, or no, levels of cell death when contacted with the same given agent or compound. It has thus been observed that while GSCs from certain individuals should be characterized as being suitable for treatment with a given chemical agent or compound, GSCs from other individuals should be characterized as being not suitable for treatment with the same agent or compound.

It has still further been surprisingly observed that, among groups of GSC cultures derived from numerous individual subjects that should all be characterized as suitable for treatment with a single chemical agent or compound, the potential suitability of such GSC cultures (and thus the GBM tumor from which they are derived) for treatment with other chemical agents or compounds varies. Thus, in some cases, where (i) aliquots of GSCs from two individuals are both observed as suggesting suitability for treatment with a first chemical agent or compound; and (ii) GSCs derived from the first individual are further observed as being suitable for treatment with a second chemical agent or compound, (iii) GSCs derived from the second individual are observed as not being suitable for treatment with the second chemical agent or compound.

It has still further been surprisingly observed that GSCs derived from a given individual (and thus the individual patient or tumor from which the GSCs are derived) may be characterized as suitable for treatment with a combination of two or more chemical agents or compounds. For example, in some cases, such a combination has been observed as having a synergistic effect in killing or inhibiting growth of the GSCs from a given individual. In some cases, although such a combination has been observed as having a particularly robust and/or synergistic effect upon GSCs derived from one individual, that combination has not been observed as having the same effect on GSCs derived from other individuals.

There exist thousands of chemical agents or compounds known or suspected to have medicinal utility and/or to be chemotherapeutic agents. In view of the surprising observations discussed above, among these thousands of compounds, one or more particular combinations of chemical agents or compounds will be particularly effective in treating some individual GBM patients (e.g. by, upon administration to the individual, killing or inhibiting growth of GSCs remaining after surgical treatment and thus preventing tumor recurrence). Further, in some cases, while such a combination of chemical agents or compounds will be particularly, even synergistically, effective in treating some GBM patients, the same combination will be relatively, or completely, ineffective in treating other GBM patients.

It has thus been observed that GSCs derived from different individuals generally respond differently to treatment with different known or suspected chemical agents or compounds. Thus, different individual GBM patients will respond differently to treatment with different combinations of chemical agents or compounds. Put another way, it has thus been observed that, among the GBM patient population, the likelihood that a particular chemical agent or compound, or combination of agents or compounds, will be effective in preventing or delaying tumor recurrence will vary from individual to individual.

To date it has been impossible to predict with an acceptable degree of certainty whether a given GBM patient is likely to respond relatively (to the population in general) well or poorly with treatment with a particular chemical agent or compound or combination of such agents or compounds. No known observable physical, physiological, genetic, or other characteristics of GBM patients, their GBM tumors, or the GSCs of such patients, have been observed as correlating with that patient's (or her tumor's or GSCs') suitability for treatment with a particular chemical agent or compound, as compared to other agents or combinations. Thus, no previously known means have provided health care practitioners with any guidance as to whether any particular chemotherapy regimen is more or less likely than another to prevent GBM tumor recurrence in any given individual. As a result, the current standard of care is to administer generally the same chemotherapy regime to all GBM patients, despite the observed variability among the population disclosed herein.

Accordingly, to date, only a guess-and-check form of testing would have provided the practitioner with information as to the suitability of a given chemotherapy regimen for treating a given individual. However, since tumor recurrence generally occurs within a matter of months, and such recurrence often results in mortality within a one or two year timeframe, applying such a guess and check approach has been practically impossible: there are too many possible compounds and combinations to test, and too little time. Thus, the current standard of care does not reflect the variability among the individuals comprising the GBM population as to whether any given chemotherapeutic regimen is more or less likely to prevent tumor occurrence in each individual. Rather, the current standard of care is generally uniform, rather than individualized, among all members of the GBM population.

The present disclosure is directed to methods of rapidly characterizing GSCs derived from a given GBM patient as being susceptible to particular chemical agents or compounds, or combinations thereof, selected from among tens, hundreds, or thousands of such agents or compounds. The present disclosure is also directed to methods of characterizing such individual GBM patients as being suitable for treatment with such compounds or combinations thereof. The present disclosure is also directed to panels of chemical agents or compounds, each of which has been observed to have the effect of killing or inhibiting growth of GSCs derived from at least some proportion of the GBM population.

In an embodiment of the methods disclosed herein, as set forth in FIG. 1, a GBM tumor is surgically resected from a GBM patient. Next, all or a portion of the resected tumor tissue (e.g., a one $mm^2$ cube) is mechanically and enzymatically digested until a suspension of individual cells is obtained. This suspension of individual cells is then propagated in stem cell culture medium, and a culture of GSCs from the individual GBM patient is thus obtained. In an embodiment, the number of GSCs obtained is sufficient to provide a target number of aliquots to be contacted with individual compounds to be selected from a panel of compounds which may be known or suspected to have anti-GBM activity. In an embodiment, the number of GSCs cultured from an individual tumor exceeds two million. In an embodiment, approximately two to three million or two to four million GSCs are cultured over a period of three to six weeks.

The obtained GSCs are then seeded into 384 well plates as aliquots of approximately 1000 cells/well. Each aliquot is then contacted with an individual compound selected from a panel of compounds which may be known or suspected to have anti-GBM activity. Cell death is then measured in each aliquot by means known to those skilled in the art. Aliquots exhibiting a threshold level of cell death (e.g., more than 50% cell death) are then identified, and the corresponding anti-GBM compounds are thus identified as potentially suitable for treating the GSCs, and thus the individual and tumor from which those GSCs were derived.

Next, a second set of GSC aliquots is contacted with one or more combinations of the compounds identified above. Cell death is again observed in each of the second set of aliquots, in order to determine which among the tested combinations cause relatively high, or synergistic, levels of GSC death.

Based on the results observed in the steps described above, the GSCs are characterized as being susceptible to treatment with given identified compounds or combinations thereof, and the GBM patient is thus characterized as being suitable for treatment with such identified compounds or combinations.

In some embodiments, information summarizing the characterization of the GSCs and/or the GBM patient is provided to a practitioner, for example the primary caregiver of the GBM patient, and the practitioner then uses such information to develop and/or administer a chemotherapy regimen to the patient.

In some embodiments, one or more of the steps of aliquoting GSCs, contacting the aliquots with the compounds or combinations, and observing the resulting level of cell death, is/are performed by use of automated robots adapted to perform such steps. In this manner, rapid, high throughput screening or testing of compounds and combinations thereof is achieved. In some embodiments, aliquots of one GSC culture may be tested against a panel of up to 200 compounds in one week.

It has been surprisingly observed that GSCs derived from different individual GSC patients vary substantially in terms of certain physiological traits, including proliferative potential, tumor-initiating ability, and therapeutic response, suggesting possible reasons for their resistance to eradication. Particularly, GSC cultures derived from some patients have been observed to grow faster than GSC cultures derived from others, when each culture is grown under comparable or identical stem cell culturing conditions. The observed differences in growth rates among GSC cultures derived from different individuals is thought to be a result of factors including both the degree of tumor necrosis (caused by radiation and/or chemotherapy having been administered to the patient prior to tumor resection) and the subtype of the tumor (samples obtained from more aggressive tumor subtypes have been observed to result in faster growing GSC cultures).

In order to characterize GSCs that result in slower-growing cultures, longer time periods are required in order to produce a sufficient volume of cell culture containing a sufficient number of GSCs so as to provide a sufficient number of aliquots to allow testing of a complete panel of potentially anti-GBM chemical agents or compounds. By contrast, faster-growing GSCs may be characterized in shorter periods of time. For example, it has been observed that, in the case of GSCs obtained from some GBM patients, GSC culturing occurs sufficiently slowly that 10 weeks or more may be required in order to culture a quantity of cells sufficient to provide an adequate number of aliquots to allow testing of 100 agents or compounds. Since the time to tumor recurrence is limited in many GBM patients, methods involving smaller panels of compounds, and thus requiring smaller numbers of aliquots, and thus reduced numbers of GSCs, provide the advantage of shorter culturing times and thus faster GSC characterization.

In short, the use of panels comprising relatively smaller numbers of compounds results in a correspondingly smaller number of aliquots of GSC culture to be contacted (and in which to observe levels of cell death). Thus, through the use of the panels disclosed herein, which comprise relatively smaller numbers of chemotherapeutic agents or compounds, smaller numbers of GSCs will be required, and thus shorter GSC culturing times will be required, allowing for faster characterization of the GSCs and more rapid development of a recommended chemotherapeutic regimen for the GBM patient from whom the GSCs are derived.

It has been surprisingly observed that, among thousands of known or suspected anti-cancer or chemotherapeutic agents or compounds, many cause little or no cell death to GSCs. However, it has also been observed that relatively small numbers of chemotherapeutic compounds, for example about 200, about 100, about 70, or fewer compounds, have all been observed to cause relatively high levels of cell death in GSCs derived from at least some proportion of the overall GBM patient population. Thus, panels comprising at least some of these about 200, 100, or 70 observed anti-GBM compounds may be used to accurately characterize GSCs derived from individual GBM patients, and thus to characterize those patients, as being suitable for treatment with one, two, three, four, or more compounds selected from such a panel. That is, among the thousands of known or suspected anti-cancer compounds, the panels of compounds disclosed herein, which in some embodiments comprise as few as about 200, 100, 70 or fewer compounds, contain a sufficiently high proportion of compounds that are all effective in killing or inhibiting growth of at least some types of GSCs, that these panels may be used to develop chemotherapeutic treatment recommendations for prevention of tumor recurrence in the majority of observed GSC types (and thus for the majority of the observed GBM population).

In an embodiment, the panel of compounds that have been observed to have anti-GSC effects in at least some GBM patients, and are thus used to contact the aliquots of GSCs disclosed in the methods herein, comprises anti-neoplastic, chemotherapeutic, and other compounds. In some embodiments, the panel comprises 76 compounds. In one embodiment, the panel contains 50, 55, 60, 65, 70, 75, 77, 78, 79, or 80 compounds. In an embodiment, the panel contains 85, 90, 95, or 100 compounds. In some embodiments, each of the compounds has a half maximal inhibitory concentration ($IC_{50}$) calculated from the methods described herein.

In an embodiment, the panel comprises at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, or all, of the following compounds: AZD-7762; AZD-8055; BEZ-235; BGT-226; MG-132; NVP-AUY-922; obatoclax; PIK-75; PKI-587; staurosporine; YM155; 10-hydroxycamptothecin; anisomycin; β-peltatin; emetine; gambogic acid; mebendazole; ouabain; peruvoside; phenethyl caffeate; podophyllin acetate; pyrvinium pamoate; and thiram.

In an embodiment, the panel further comprises at least one of the following compounds: albendazole, aprepitant, atorvastatin calcium, auraofin, bleomycin, bortezomib, brompheniramine maleate, captopril, carboplatin, celecoxib, chloroquine, cidovofir, cladribine, clofarabine, clofazimine, clomipamine, clonidine, colchicine, cyclophosphamide, cytarabine, dactinomycin, daunorubicin, digoxin, disulfiram, docetaxel, doxorubicin, erlotinib, ethacrynic acid, epirubicin, etoposide, fludarabine phosphate, fluorouracil, fluphenazine, fluvastatin, gemcitabine, haloperidol, homoharringtonine, hydroxychloroquine, idarubicin, irinotecan, itraconazole, ketoconazole, lomustine, lovastatin, mefloquine, melphalan, memantine, metformin, methotrexate, methylene blue, minoxidil, mitomycin C, mitoxantrone, mycophenolate mofetil, nelfinavir, nisoldipine, paclitaxel, pindolol, pitavastatin, rosuvastatin calcium, sertaline, simvastatin, sirolimus, sorafenib, sodium tetradecyl sulfate, sunitinib, temozolomide, teniposide, topotecan, trifluoperazine, valganciclovir, valproic acid, vinblastine sulfate, vincristine sulfate, vinorelbine and vorinostat.

In an embodiment, the panel comprises at least 10 of the following anti-neoplastic/chemotherapeutic compounds: bortezomib, clofarabine, cytarabine, dactinomycin, daunorubicin, doxorubicin, erlotinib, epirubicin, etoposide, fludarabine phosphate, gemcitabine, irinotecan, melphalan, methotrexate, mitomycin C, mitoxantrone, paclitaxel, sorafenib, sunitinib, temozolomide, teniposide, topotecan, vinblastine sulfate, vincristine sulfate and vinorelbine; at least 10 of the following compounds: albendazole, aprepitant, atorvastatin calcium, auraofin, celecoxib, chloroquine, cidovofir, clofazimine, clomipamine, clonidine, colchicine, digoxin, fluphenazine, fluvastatin, haloperidol, homoharringtonine, itraconazole, lovastatin, mefloquine, metformin, methylene blue, minoxidil, mycophenolate mofetil, nelfinavir, pindolol, rosuvastatin calcium, sertaline, simvastatin, sirolimus, sodium tetradecyl sulfate, trifluoperazine, valganciclovir, valproic acid and vorinostat, and disulfiram.

In an embodiment, panels of compounds disclosed herein are manufactured for use in characterizing GSCs and/or GBM tumors or patients, in terms of the suitability of such GBMS or patients for treatment with one or more compounds from the panel.

The step of culturing GSCs in embodiments of methods disclosed herein is performed by methods known to those skilled in the art, for example the methods described in Cobbs et al., METHODS IN MOLECULAR BIOLOGY 1119:165-96 (2014) and Pollard et al., Cell Stem Cell 4(6): 568-80 (2009). The cells may be cultured in a nutritive composition that supports the cultivation and/or growth of cells, referred to as a "cell culture medium." The cell culture medium may be a complete formulation, i.e., a cell culture medium that requires no supplementation to culture cells or the cell culture medium may be an incomplete formulation, i.e., a cell culture medium that requires supplementation. In one embodiment the stem cell culture medium is NEUROCULT NS-A proliferation medium (Stemcell Technologies, Vancouver, BC, Canada) or NEUROBASAL medium (Life Technologies, Carlsbad, Calif.). The dissociation enzyme is ACCUTASE (Life Technologies, Carlsbad, Calif.), an enzyme mixture with proteolytic and collagenolytic enzyme activity, although any dissociation enzyme that disrupts bonding between individual cells is envisioned. Further, combinations of mechanical (e.g., mincing, sieving, or scratching off), chemical (e.g., in the absence of divalent cations), and enzymatic (e.g., digesting with ACCUTASE, collagenase, trypsin, papain, elastase, pronase, hyaluronidase, or selected combinations) dissociation may be used in the methods described herein. Mechanical disruption of the tumor tissue may be performed prior to addition of the dissociation enzyme. In an embodiment, mechanical disruption includes cutting with sterile scalpels or pipetting with bores of decreasing size.

The $IC_{50}$ is a measure of the effectiveness of a substance in inhibiting a specific biological or biochemical function and can be determined by constructing a dose-response curve and examining the effect of different concentrations of compounds on GSC death. In an embodiment, an 8 point dose-responsive curve for each compound (repeated twice) is tested (16 wells per compound). In an embodiment, GSC death is determined by a luciferase assay, and other means known in the art are also suitable for determining cell death.

In an embodiment, characterization of a given GSC, GBM tumor or patient as being suitable with a given compound is determined by weighing a number of characteristics of the compound itself. In one embodiment, the threshold cell death percentage for characterization of a compound as a therapeutic for treating a patient is 50%. In some embodiments, potency (the overall percentage of cell death) is balanced with variance (the effectiveness of a given compound across multiple tumors) when considering suitability of a given compound. Additional factors can include overall $IC_{50}$, the compound's properties (including its propensity to cross the blood brain barrier), and side effects of the compound. In an embodiment, a combination of two, three, or more compounds are identified as being potentially effective for treating a patient, it is confirmed that the compounds are not toxic in combination, and that patient is then characterized as being suitable for treatment with that combination. In another embodiment, one compound is an anti-neoplastic/chemotherapeutic compound in combination with two other compounds. In another embodiment, disulfiram is one of the members of the combination of compounds.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a patient having a glioblastoma multiforme (GBM) tumor comprising a GBM stem cell in order to extend the patient's overall survival following treatment with three or more identified compounds , comprising:
    a) culturing the GBM stem cell to provide a culture;
    b) contacting a first set of aliquots of the culture with individual compounds selected from a panel of compounds;
    c) identifying three or more of the selected compounds that cause more than a threshold level of cell death in the first set of aliquots;
    d) characterizing the patient having the GBM tumor comprising the GBM stem cell as suitable for treatment with one or more combinations comprising the three or more identified compounds; and
    e) administering one or more combinations comprising the three or more identified compounds to the patient, thereby treating the patient having the GBM tumor
    wherein the panel comprises at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, or all, of the following compounds: AZD-7762; AZD-8055; BEZ-235; BGT-226; MG-132; NVP-AUY-922; obatoclax; PIK-75; PKI-587; staurosporine; YM155; 10-hydroxycamptothecin; anisomycin; β-peltatin; emetine; gambogic acid; mebendazole; ouabain; peruvoside; phenethyl caffeate; podophyllin acetate; pyrvinium pamoate; and thiram, and
    wherein the panel further comprises at least one of: auranofin, bortezomib, colchicine, digoxin, disulfiram, methotrexate, pitavastatin, sertraline, valganciclovir, and vincristine sulfate; and wherein the panel further comprises one or more of the following compounds: albendazole, aprepitant, atorvastatin calcium, bleomycin, brompheniramine maleate, captopril, carboplatin, celecoxib, chloroquine, cidofovir, cladribine, clofarabine, clofazimine, clomipramine, clonidine, cyclophosphamide, cytarabine, dactinomycin, daunorubicin, docetaxel, doxorubicin, erlotinib, ethacrynic acid, epirubicin, etoposide, fludarabine phosphate, fluorouracil, fluphenazine, fluvastatin, gemcitabine, haloperidol, homoharringtonine, hydroxychloroquine, idarubicin, irinotecan, itraconazole, ketoconazole, lomustine, lovastatin, mefloquine, melphalan, memantine, metformin, methylene blue, minoxidil, mitomycin C, mitoxantrone, mycophenolate mofetil, nelfinavir, nisoldipine, paclitaxel, pindolol, rosuvastatin calcium, simvastatin, sirolimus, sorafenib, sodium tetradecyl sulfate, sunitinib, temozolomide, teniposide, topotecan, trifluoperazine, valproic acid, vinblastine sulfate, vinorelbine and vorinostat,
    wherein the patient has completed a standard of care therapy comprising radiation and temozolomide (TMZ).

2. The method of claim 1, wherein the GBM stem cell is derived from a GBM tumor tissue, and wherein the culturing step (a) comprises:

i) adding one or more dissociation enzymes to the GBM tumor tissue;

ii) incubating the GBM tumor tissue to facilitate digestion of the GBM tumor tissue by the one or more enzymes;

iii) obtaining a suspension of cells from the digested GBM tumor tissue; and iv) propagating the suspension of cells in stem cell culture medium to provide the culture.

3. The method of claim 2, wherein the dissociation enzyme is an enzyme mixture with proteolytic and collagenolytic enzyme activity.

4. The method of claim 2, wherein the incubating takes place at a temperature range between 35° C. and 39° C.

5. The method of claim 4, wherein the incubating takes place at about 37° C.

6. The method of claim 1, wherein the threshold level is about 50%.

7. The method of claim 1, wherein at least one of the one or more combinations comprises at least one anti-neoplastic/chemotherapeutic compound and at least one additional compound.

8. The method of claim 1, wherein step (c) further comprises:

from the identified three or more selected compounds, further selecting at least two compounds as preferred compounds based on at least one of the following characteristics:

overall level of cell death caused in the first set of aliquots;

known ability to cross the blood-brain barrier in a GBM patient; and known likely side effects to a GBM patient, and wherein step (d) further comprises characterizing the GBM stem cell as suitable for treatment with one or more combinations of the preferred compounds.

\* \* \* \* \*